United States Patent
Olsen

(10) Patent No.: US 9,629,928 B1
(45) Date of Patent: Apr. 25, 2017

(54) HASH-BASED INVENTORY IDENTIFICATION

(75) Inventor: Larry David Olsen, Lindon, UT (US)

(73) Assignee: Symantec Corporation, Mountain View, CA (US)

( * ) Notice: Subject to any disclaimer, the term of this patent is extended or adjusted under 35 U.S.C. 154(b) by 1103 days.

(21) Appl. No.: 12/059,391

(22) Filed: Mar. 31, 2008

(51) Int. Cl.
*G06Q 10/00* (2012.01)
*G06F 15/177* (2006.01)
*G01R 31/28* (2006.01)
*A61K 48/00* (2006.01)

(52) U.S. Cl.
CPC .................................. *A61K 48/00* (2013.01)

(58) Field of Classification Search
USPC .......................................................... 705/28
See application file for complete search history.

(56) References Cited

U.S. PATENT DOCUMENTS

| | | | |
|---|---|---|---|
| 6,220,768 B1* | 4/2001 | Barroux | H04L 41/0213 709/224 |
| 6,360,260 B1* | 3/2002 | Compliment | H04L 41/0213 709/223 |
| 6,470,387 B1* | 10/2002 | Fischer | H04L 29/06 709/224 |
| 6,490,617 B1* | 12/2002 | Hemphill | H04L 41/0213 709/223 |
| 7,185,075 B1* | 2/2007 | Mishra | H04L 12/24 379/207.01 |
| 2001/0056386 A1* | 12/2001 | O'Halloran | G06F 11/2289 705/28 |
| 2002/0010659 A1* | 1/2002 | Cruse | G06Q 10/087 705/28 |
| 2002/0073329 A1* | 6/2002 | Brombal | G06Q 10/087 726/26 |
| 2002/0133573 A1* | 9/2002 | Matsuda | H04L 12/24 709/220 |
| 2003/0061315 A1* | 3/2003 | Jin | H04L 67/16 709/220 |

(Continued)

*Primary Examiner* — Ashford S Hayles
(74) *Attorney, Agent, or Firm* — Patent Law Works LLP

(57) ABSTRACT

A mechanism for providing inventory information from distributed computing resources in an enterprise network in a manner that minimizes network traffic being sent from those computing resources to a centralized inventory server is provided. Bandwidth minimization is performed by generating a value corresponding to identifying information for each item inventoried on a computing resource and transmitting only those values to the inventory server. The generated value is shorter than a string containing the detailed information regarding the inventoried item, but is unique to that item. The inventory server then only requests more detailed information about an individual inventory item if a reported value has not previously been reported to the inventory server. In this manner, detailed information about a specific inventoried item is only transmitted through the network the first time that the item is inventoried and reported from any computer in the network. For any subsequent nodes reporting the same inventoried item, only the value is transmitted through the network and recorded within the inventory server. This avoids transmitting detailed information about each inventoried item for each computer during each computer report to an inventory server, thereby reducing network traffic.

21 Claims, 6 Drawing Sheets

(56) References Cited

U.S. PATENT DOCUMENTS

| | | | |
|---|---|---|---|
| 2003/0133556 A1* | 7/2003 | Naik | H04L 41/044 379/201.12 |
| 2003/0200294 A1* | 10/2003 | Thorpe | H04L 12/24 709/223 |
| 2004/0093408 A1* | 5/2004 | Hirani | H04L 41/12 709/224 |
| 2005/0002380 A1* | 1/2005 | Miller | H04L 41/12 370/352 |
| 2005/0254438 A1* | 11/2005 | Turk | H04L 41/0869 370/254 |
| 2005/0262226 A1* | 11/2005 | Holloway | G08C 19/28 709/221 |
| 2006/0064619 A1* | 3/2006 | Wen | G06F 9/50 714/734 |
| 2006/0091207 A1* | 5/2006 | Chang | G06Q 10/087 235/385 |
| 2006/0091999 A1* | 5/2006 | Howarth | G06K 17/00 340/10.3 |
| 2006/0103504 A1* | 5/2006 | Vassallo | G06Q 10/06 340/5.92 |
| 2006/0129415 A1* | 6/2006 | Thukral | G06Q 10/087 705/28 |
| 2006/0178954 A1* | 8/2006 | Thukral | G06Q 10/087 705/28 |
| 2007/0061227 A1* | 3/2007 | Gimpl | G06Q 10/087 705/28 |
| 2007/0113289 A1* | 5/2007 | Blumenau | G06F 17/30085 726/26 |
| 2007/0130218 A1* | 6/2007 | Blumenau | G06F 17/30011 |
| 2007/0139231 A1* | 6/2007 | Wallia | H04L 63/1408 341/50 |
| 2007/0239569 A1* | 10/2007 | Lucas | G06Q 10/08 705/28 |
| 2008/0049644 A1* | 2/2008 | Halbert | H04L 41/12 370/254 |
| 2008/0070495 A1* | 3/2008 | Stricklen | H04W 8/22 455/3.01 |
| 2008/0120200 A1* | 5/2008 | Hurtis | G06Q 10/087 705/28 |
| 2008/0162308 A1* | 7/2008 | Sharma | G06Q 10/087 705/28 |
| 2008/0189405 A1* | 8/2008 | Zarenin | H04L 12/2602 709/224 |
| 2008/0256354 A1* | 10/2008 | Blumenau | G06F 17/30997 713/153 |
| 2009/0052461 A1* | 2/2009 | Brown | H04L 12/4625 370/401 |
| 2009/0119414 A1* | 5/2009 | Estrada | H04L 29/12009 709/245 |
| 2009/0238079 A1* | 9/2009 | Gantenbein | H04L 12/24 370/241 |
| 2010/0030777 A1* | 2/2010 | Panwar | G06Q 10/087 707/600 |
| 2010/0042708 A1* | 2/2010 | Stamler | G06Q 10/087 709/221 |
| 2010/0312597 A1* | 12/2010 | Ellisor, Jr. | G06Q 10/06375 705/7.37 |
| 2014/0149416 A1* | 5/2014 | Wallace | G06F 17/30598 707/737 |

* cited by examiner

HASH-BASED INVENTORY IDENTIFICATION

FIELD OF THE INVENTION

The present invention relates to inventory management in a computer network, and particularly to a system and method for providing inventory information for hardware and software installed on computers in a network to a centralized server in an efficient manner.

BACKGROUND OF THE INVENTION

An ever-increasing reliance on information and the computing systems that produce, process, distribute, and maintain such information in its various forms, continues to put great demands on techniques for providing up-to-date information about available computing resources to a user. As the number of computing resources (e.g., desktop PCs, notebook PCs, server-class PCs and workstations, as well as attached storage and memory resources) increases in an enterprise, an increasing amount of system administration resources have to be expended in order to track those computing resources. Information related to the hardware installed on the various computing resources, as well as installed software, is highly desirable but also difficult to track in a fluid environment.

One method of tracking inventory information related to available computing resources includes sending system management employees to each available computing resource and manually taking an inventory of both the hardware and software installed. However, as the number of computing resources increases and as their geographical locations disburse, such manual inventory taking can expend a significant amount of system management resources in both time and money.

Alternatively, automated inventory systems can be used to scan each computing resource in a network and provide information related to installed hardware and software to a centralized inventory server. Typically, such automated systems can report detailed information over the network about each hardware and software item found on a computing node. But, as the number of computing resources increases in the enterprise network, the network traffic generated by transmitting detailed information about each inventoried item on each computing resource can consume a significant amount of network bandwidth and server resources (e.g., CPU, memory, disk space, and the like). This consumption of available network bandwidth can adversely impact the utility of the network for business-related computing needs.

It is therefore desirable to provide an automated computer resource inventory system that minimizes the amount of network bandwidth consumed by transmitting inventory information to an inventory repository. By decreasing such network traffic, more frequent inventory scanning can be taken of an enterprise's computing resources, thereby providing a more accurate picture of available computing resources.

SUMMARY OF THE INVENTION

A method and apparatus for providing inventory information from distributed computing resources in an enterprise network in a manner that minimizes network traffic being sent from those computing resources to a centralized inventory server is provided. Bandwidth minimization is performed by generating a value corresponding to identifying information for each item inventoried on a computing resource and transmitting only those values to the inventory server. The generated value is shorter than a string containing the detailed information regarding the inventoried item, but is unique to that item. The inventory server then only requests more detailed information about an individual inventory item if a reported value has not previously been reported to the inventory server. In this manner, detailed information about a specific inventoried item is only transmitted through the network the first time that the item is inventoried and reported from any computer in the network. For any subsequent nodes reporting the same inventoried item, only the value is transmitted through the network and recorded within the inventory server. This avoids transmitting detailed information about each inventoried item for each computer during each computer report to an inventory server, thereby reducing network traffic.

Embodiments of the present invention provide for receiving inventory information from a remote node, determining if a first inventory item value in the inventory information is not previously stored in an inventory item list, requesting that identifying information for the first inventory item value be provided by the remote node, and storing the first inventory item value and the identifying information in the inventory item list. In one aspect of the present invention, each inventory item value uniquely identifies a corresponding item on the remote node. In another aspect of the present invention, each inventory item value is generated using information uniquely identifying the corresponding item on the remote node. In a further aspect of the present invention, each inventory item value is generated using a hash function. In another aspect of the present invention, the inventory item values associated with the remote node are stored with a unique identifier for the remote node.

BRIEF DESCRIPTION OF THE DRAWINGS

The present invention may be better understood, and its numerous objects, features and advantages made apparent to those skilled in the art by referencing the accompanying drawings.

DETAILED DESCRIPTION

The present invention provides a mechanism for providing inventory information from distributed computing resources in an enterprise network in a manner that minimizes network traffic being sent from those computing resources to a centralized inventory server. Embodiments of the present invention perform such bandwidth minimization by generating a value corresponding to identifying information for each item inventoried on a computing resource and transmitting only those values to the inventory server. The generated value is shorter than a string containing the detailed information regarding the inventoried item, but is unique to that item. The inventory server then only requests more detailed information about an individual inventory item if a reported value has not previously been reported to the inventory server. In this manner, detailed information about a specific inventoried item is only transmitted through the network the first time that the item is inventoried and reported from any computer in the network. For any subsequent nodes reporting the same inventoried item, only the value is transmitted through the network and recorded within the inventory server. This avoids transmitting detailed information about each inventoried item for each computer during each computer report to an inventory server, thereby reducing network traffic.

Figure 1:
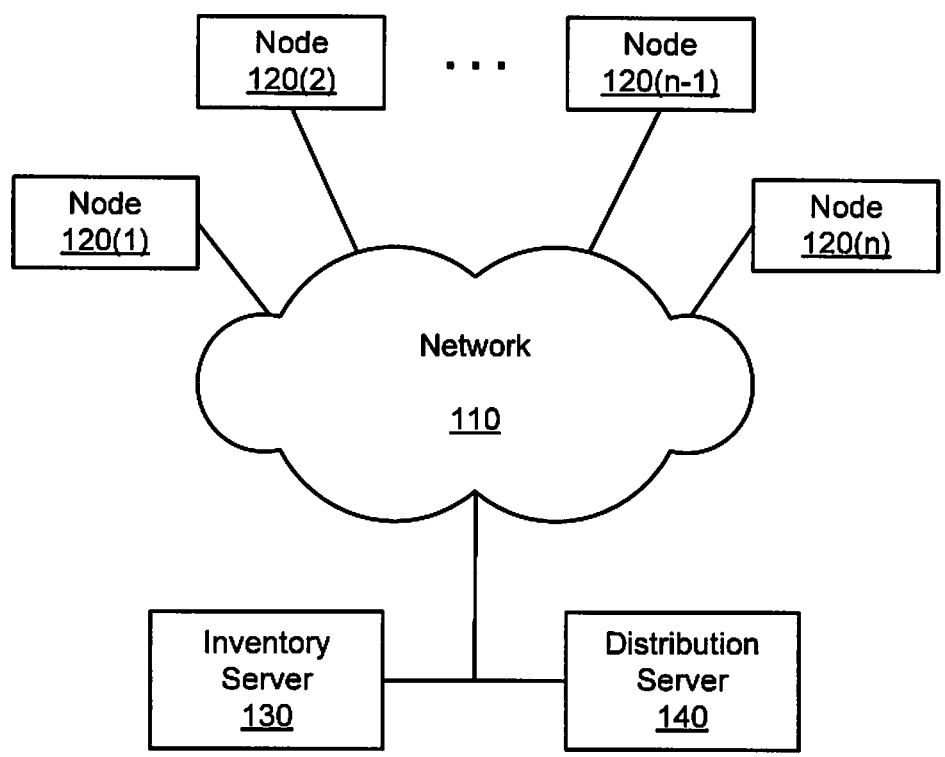
FIG. 1 is a simplified block diagram of a network environment suitable for deploying implementations of the present invention.

FIG. 1 is a simplified block diagram of a network environment suitable for deploying implementations of the present invention. A network 110 provides connection to distributed computing resources 120(1)-120(n). These distributed computing resources can include a heterogeneous set of network nodes, including, for example, desktop PCs, workstations, laptop computers, server-class computers, and the like. Network 110 can service one or more geographic locations associated with an enterprise.

Network 110 is further coupled to an inventory server 130. Inventory server 130 is configured to receive inventory information regarding computing resources 120(1)-(n). Inventory server 130 can then store the inventory information in one or more databases or database tables to be used for tracking and analysis by administrators of the enterprise network.

The inventory information collected by inventory server 130 can be used by system administrators for a variety of purposes. For example, systems administrators can use the software inventory information to determine those software items in the network that are in need of upgrading on individual machines. Hardware inventory information can be used, for example, to identify those compute nodes that have minimum essential hardware to install certain types of software. An inventory server can also group various computers based upon their reported inventory and then assign jobs or tasks to those identified computers that are appropriate for the reported inventory (e.g., a software upgrade to all compute nodes having sufficient memory, an appropriate processor, and an older version of the software to be upgraded). FIG. 1 illustrates a distribution server 140 that can be configured to use information provided by the inventory server to transmit software distribution packages to identified computing resources.

Figure 2:
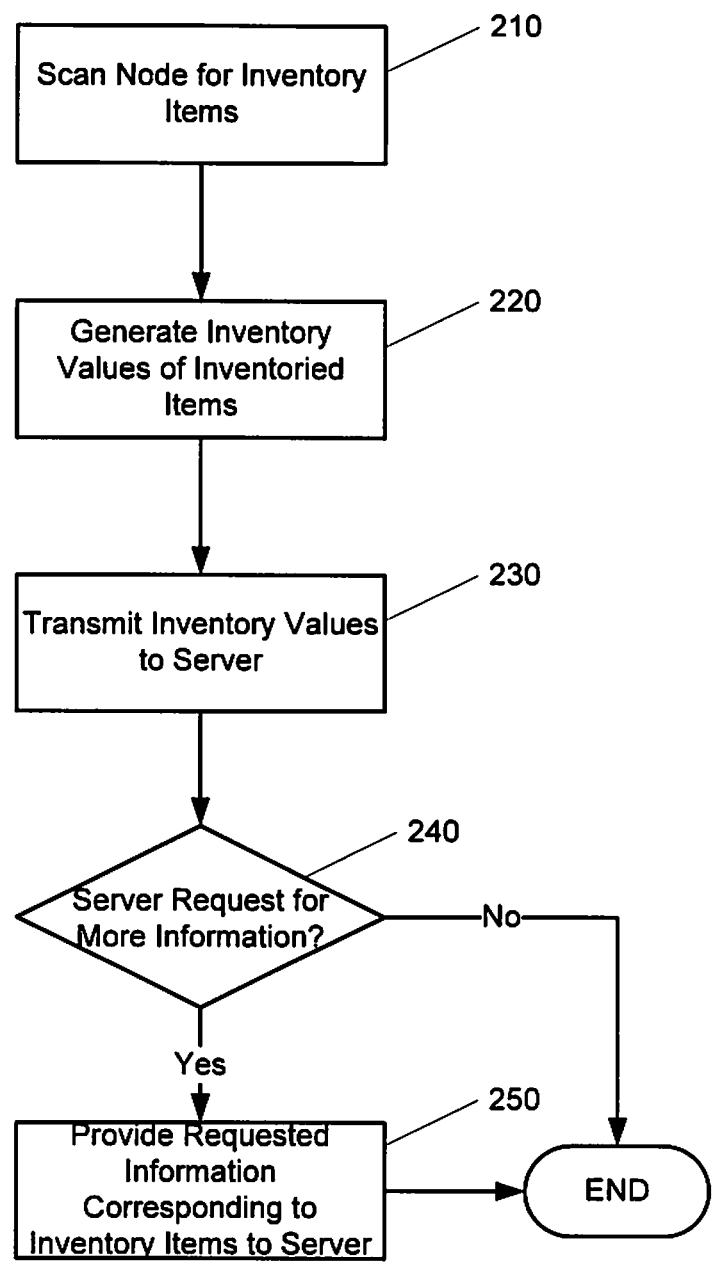
FIG. 2 is a simplified flow diagram illustrating an inventory process taken on a compute node, in accord with embodiments of the present invention.

FIG. 2 is a simplified flow diagram illustrating an inventory process taken on a compute node, in accord with embodiments of the present invention. In order to provide the inventory information to the inventory server, each of the computing resources 120(1)-(n) can execute inventory software on that node that scans the node for software and hardware resources and then provides information about those scanned resources to the inventory server over the network. The scan will be conducted of the compute node for all or a selected subset of hardware and software inventory items (210). During the scan, sufficient information is gathered about the inventoried items to uniquely identify each inventoried item. For example, for software information such as the name of the software, the manufacturer of the software, and a version number for the software (e.g., file version or product version) can be collected. For hardware a unique device identifier can be collected for each installed hardware item (e.g., a plug-and-play device identifier).

An inventory value can then be generated from the unique information collected for each inventoried item (220). One embodiment of the present invention generates the inventory values using a hash function. The inventory values are shorter than the complete length of the unique inventory information used to generate the values. A generated hash value can be, for example, an integer value or a GUID-type value. Although typically longer than an integer value, GUID-type hash values are used by embodiments of the present invention because there is a significantly reduced chance of GUID duplication for different unique inventoried items.

Once the inventory values are generated, the node can then transmit the inventory values for the inventoried items to the inventory server along with a unique identifier for the compute node itself (230). In order to accurately reflect the distribution of resources in the enterprise, each resource reporting inventory must be uniquely identified. Such a unique identifier can be generated, for example, using information such as the serial number associated with the computing resource (e.g., from the computer's BIOS), a universal unique identifier (UUID) associated with the compute node, and a MAC address associated with the network interface card of the compute node. As much of this information can be collected as needed to uniquely identify the compute node against all others within the network. A node identifier (e.g., a hash value) corresponding to this identification information can then also be generated and that node identifier value is associated with the inventoried information.

Once the inventory software on the compute node has provided the inventory information to the inventory server, the inventory software can then wait for a request for more information from the inventor server (240). Should the server not require any additional information, the inventory client can then terminate or wait until the next scheduled inventory time. Should the server request detailed information about any of the inventoried items, the inventory client can then provide the requested information corresponding to the hash values returned by the inventory server (250). The information provided by the inventory client can include, for example, all the information required to uniquely identify the inventoried item corresponding to the hash value (e.g., the information used in the generation of the hash value). Once the inventory software on the node has provided the information requested by the inventory server, the inventory client can terminate or wait until the next scheduled inventory time.

Figure 3:
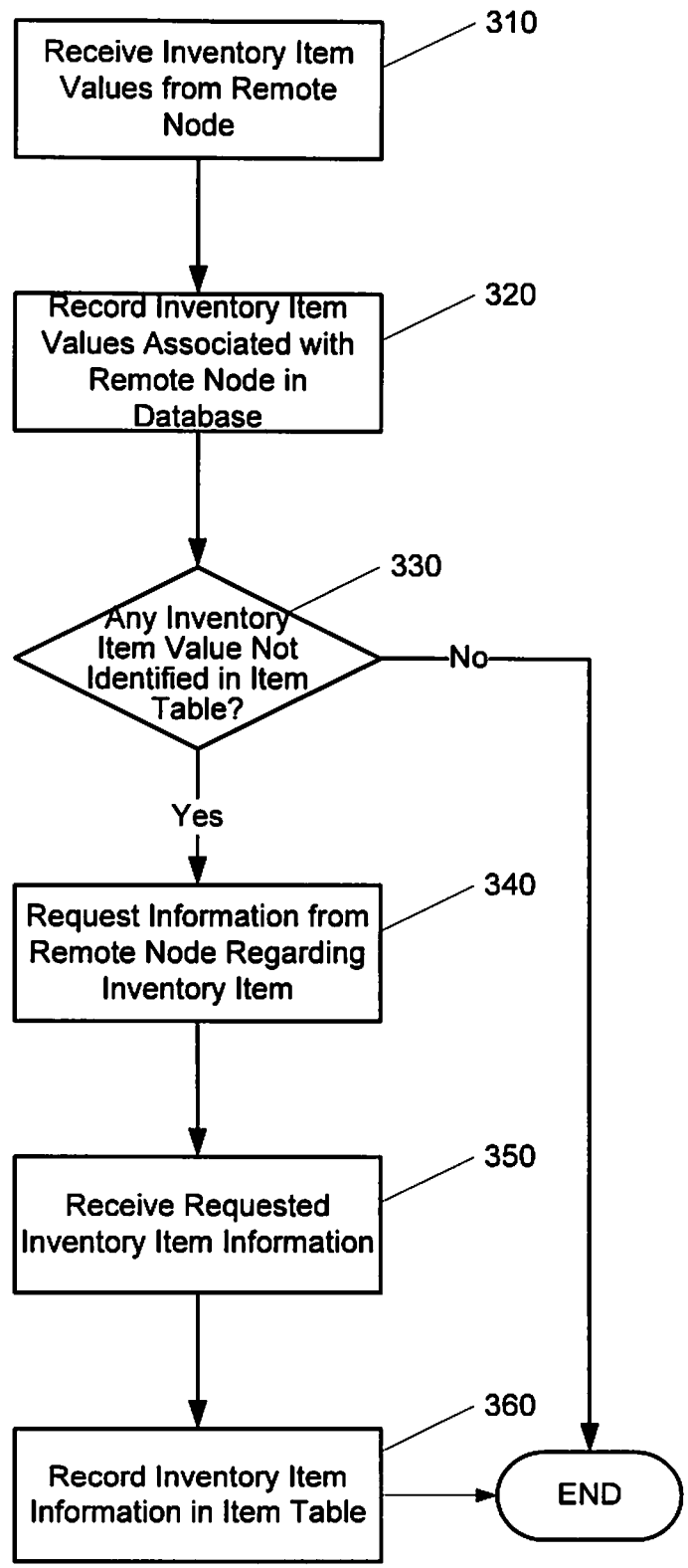
FIG. 3 is a simplified flow diagram illustrating an inventory process carried out by an inventory server (e.g., 130), in accord with embodiments of the present invention.

FIG. 3 is a simplified flow diagram illustrating an inventory process carried out by an inventory server (e.g., 130), in accord with embodiments of the present invention. The inventory server receives transmission of the inventory values (e.g., hash values) from the inventory client on a compute node (310). One example of inventory values, as discussed above, are hash values, but the invention is not limited to inventory values generated by a hash function. The inventory server can then record the inventory values corresponding to the inventoried items in a table entry associated with the unique identifier of the reporting node (320).

The inventory server can then determine if any of the reported inventory items has not previously been identified (330). Such a determination can be performed, for example, by using the reported inventory value as an index for an item table in a database. If there is no entry corresponding to the hash value, then the inventory server can request additional information from the client regarding that inventoried item (340). The inventory server can, for example, transmit to the node that reported the inventoried item a message containing the hash value and a request for information related to that inventory value. The inventory server can time such a request to take place immediately upon identifying an unknown hash value or the inventory server can collect a number of unidentified hash values and perform a batch request for information related to those hash values at a later (e.g., non-peak time). Once the inventory server receives the requested information related to the unknown hash values (350), the inventory server can record the inventoried item information, for example, in an entry in a database associated with the inventory value.

Figure 4:
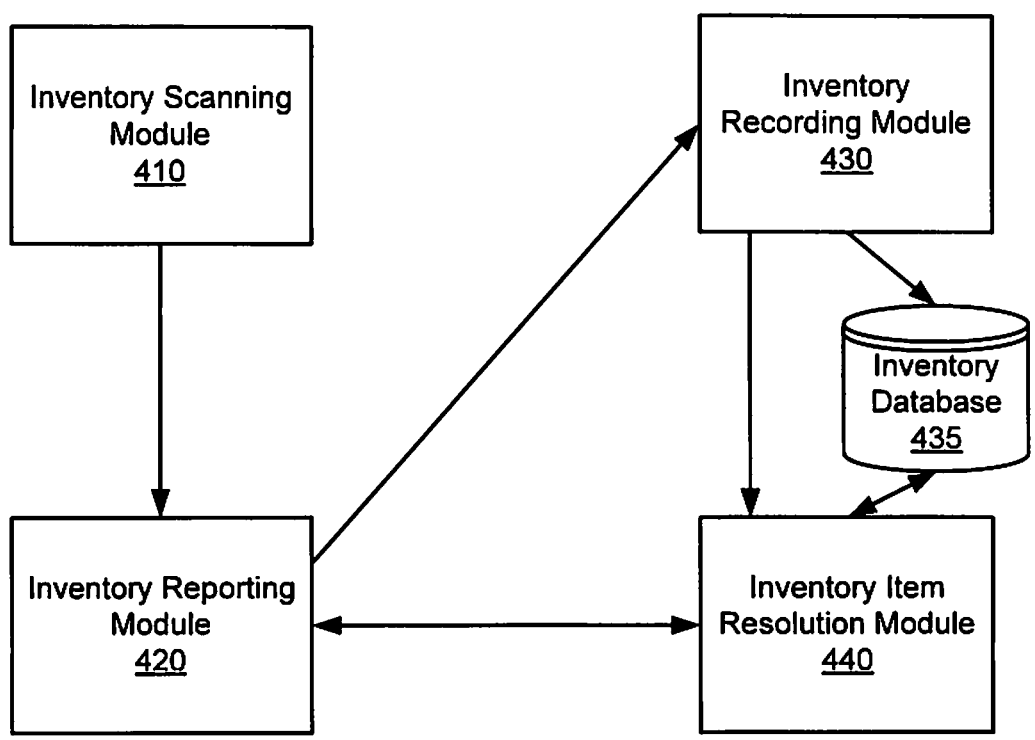
FIG. 4 is a simplified block diagram illustrating a system configured to perform tasks in accord with embodiments of the present invention.

FIG. 4 is a simplified block diagram illustrating a system configured to perform tasks in accord with embodiments of the present invention. An inventory scanning module 410 performs tasks related to scanning a compute node (e.g., node 120(1)) for inventory items. As discussed above, such inventory items can include both software and hardware installed on that node. Inventory scanning module can be an installed software on the compute node, which is either triggered to run periodically or can be set to run one time. Embodiments of the present invention provide for the inventory scanning module to be controlled remotely by a network administrator, who can thereby configure inventory scanning modules to execute across a network in a manner that causes minimal impact upon users and upon network bandwidth. Inventory scanning module 410 then provides results of the inventory scan to inventory reporting module 420. Inventory reporting module 420 is configured to maintain results of the inventory scan while providing the inventory scan results to inventory recording module 430. Inventory reporting module 420 is further configured to generate inventory values corresponding to the inventory items found in the inventory scan. In embodiments of the present invention, the inventory values are hash values of selected information that uniquely identifies the inventory items, as discussed above. Embodiments of the present invention provide for the inventory reporting module 420 to be installed on the compute node, while inventory recording module 430 can be either on the compute node or in an inventory server (e.g., inventory server 130).

Inventory recording module 430 receives the inventory values generated by inventory reporting module 420, along with a unique identifier of the compute node associated with those inventory items. Inventory recording module 430 then stores the received information in an inventory database 435. Inventory database 435 stores the inventory values and node identification information in tables, as discussed above. Inventory item resolution module 440 can then receive an indication from inventory recording module 430 that the inventory values have been stored. In response, inventory item resolution module 440 then will compare the stored inventory values from the compute node against previously stored and fully identified inventory values. If any of the inventory values from the compute node do not match any of the previously stored and identified inventory values, inventory item resolution module 440 can then request detailed information about the inventory items corresponding to the unmatched inventory values by sending a list of the unmatched inventory values to inventory reporting module 420. In embodiments of the present invention, upon receiving the request, inventory reporting module 420 will then provide the detailed information related to the inventory value to inventory item resolution module 440. In one embodiment of the present invention, inventory reporting module 420 can provide the requested information by retaining the scan results from the previous scan along with the generated inventory values. Inventory reporting module 420 can compare the requested inventory values with the retained inventory values and then provide the corresponding detailed information. Once inventory item resolution module 440 receives the detailed inventory item information, the inventory item resolution module stores the detailed information in a detailed information table in inventory database 435, as discussed above.

Using embodiments of the present invention, as described above, sufficient information to uniquely identify each inventoried item on every compute node is maintained by the inventory server. But network bandwidth is conserved because that identifying information is transmitted only by the first node to report that particular inventoried item. All subsequent nodes that have a previously reported inventoried item will only transmit an inventory value (e.g., a hash value) corresponding to that inventoried item. In addition, inventory database resources are also conserved because inventory items for each compute node are only associated with their inventory values and the full detailed information corresponding to those inventory values is only stored once, instead of repeated for each node having that item.

An additional advantage that embodiments of the present invention provide is that system administrators can schedule inventory scanning to occur with a high frequency because the reporting of inventory scanning will minimally impact network bandwidth and inventory server resources. Previous inventory recording systems in large networks may have recommended that scheduling of inventory occur only weekly and the various compute nodes be staggered in their reporting over the week in order to conserve network resources. Embodiments of the present invention can have scheduled inventory reporting more frequently (e.g., hourly), so that system administration can have a very fresh inventory of computer resources. Further, because the amount of information that is transmitted over the network is dramatically reduced, embodiments of the present invention are highly scalable in the number of nodes for which inventory can be managed.

Embodiments of the inventory server provide a current picture of the hardware and software currently installed on the compute nodes in an enterprise network. Additionally, embodiments of the present invention can also track historical inventory of hardware and software on the various nodes. For example, an inventory server can associate timestamp information with entries related to the recorded inventory values associated with the compute nodes. Through such timestamp information, the inventory information can be used to track when items were added or subtracted from the various nodes and also to track changes in installed hardware on the various compute nodes. Such information can be used, for example, to track progress of installation of new or updated software, or to aid in security checks of hardware on the various compute nodes.

An Example Computing and Network Environment

As shown above, the present invention can be implemented using a variety of computer systems and networks. An example of one such computing and network environment is described below with reference to FIGS. 5 and 6.

Figure 5:
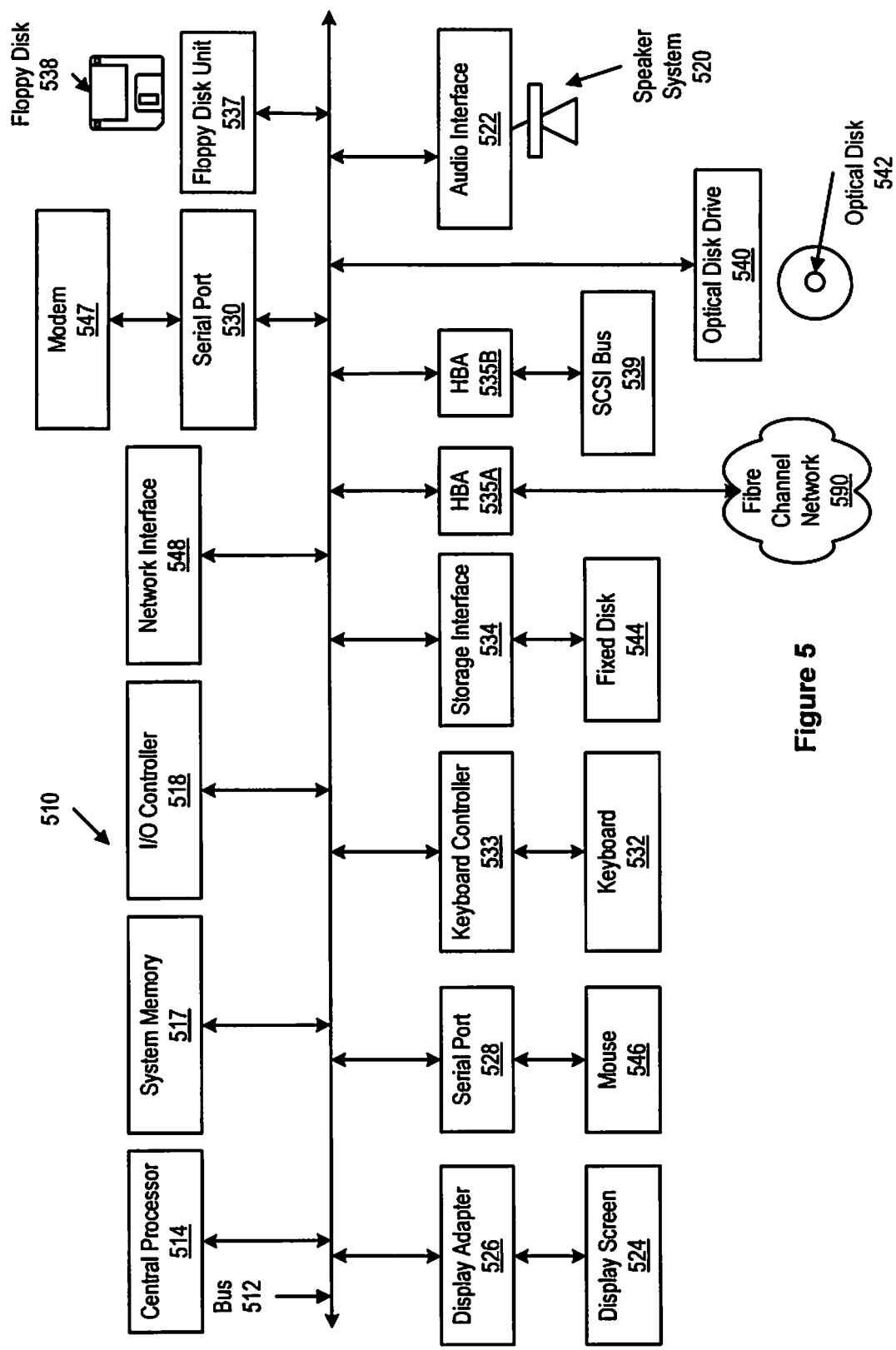
FIG. 5 depicts a block diagram of a computer system suitable for implementing embodiments of the present invention.

FIG. 5 depicts a block diagram of a computer system 510 suitable for implementing the present invention. Computer system 510 includes a bus 512 which interconnects major subsystems of computer system 510, such as a central processor 514, a system memory 517 (typically RAM, but which may also include ROM, flash RAM, or the like), an input/output controller 518, an external audio device, such as a speaker system 520 via an audio output interface 522, an external device, such as a display screen 524 via display adapter 526, serial ports 528 and 530, a keyboard 532 (interfaced with a keyboard controller 533), a storage interface 534, a floppy disk drive 537 operative to receive a floppy disk 538, a host bus adapter (HBA) interface card 535A operative to connect with a Fibre Channel network 590, a host bus adapter (HBA) interface card 535B operative to connect to a SCSI bus 539, and an optical disk drive 540 operative to receive an optical disk 542. Also included are a mouse 546 (or other point-and-click device, coupled to bus 512 via serial port 528), a modem 547 (coupled to bus 512 via serial port 530), and a network interface 548 (coupled directly to bus 512).

Bus 512 allows data communication between central processor 514 and system memory 517, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components. Applications resident with computer system 510 are generally stored on and accessed via a computer readable medium, such as a hard disk drive (e.g., fixed disk 544), an optical drive (e.g., optical drive 540), a floppy disk unit 537, or other storage medium. Additionally, applications can be in the form of electronic signals modulated in accordance with the application and data communication technology when accessed via network modem 547 or interface 548.

Storage interface 534, as with the other storage interfaces of computer system 510, can connect to a standard computer readable medium for storage and/or retrieval of information, such as a fixed disk drive 544. Fixed disk drive 544 may be a part of computer system 510 or may be separate and accessed through other interface systems. Modem 547 may provide a direct connection to a remote server via a telephone link or to the Internet via an internet service provider (ISP). Network interface 548 may provide a direct connection to a remote server via a direct network link to the Internet via a POP (point of presence). Network interface 548 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 5 need not be present to practice the present invention. The devices and subsystems can be interconnected in different ways from that shown in FIG. 5. The operation of a computer system such as that shown in FIG. 5 is readily known in the art and is not discussed in detail in this application. Code to implement the present invention can be stored in computer-readable storage media such as one or more of system memory 517, fixed disk 544, optical disk 542, or floppy disk 538. The operating system provided on computer system 510 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present invention may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 6:
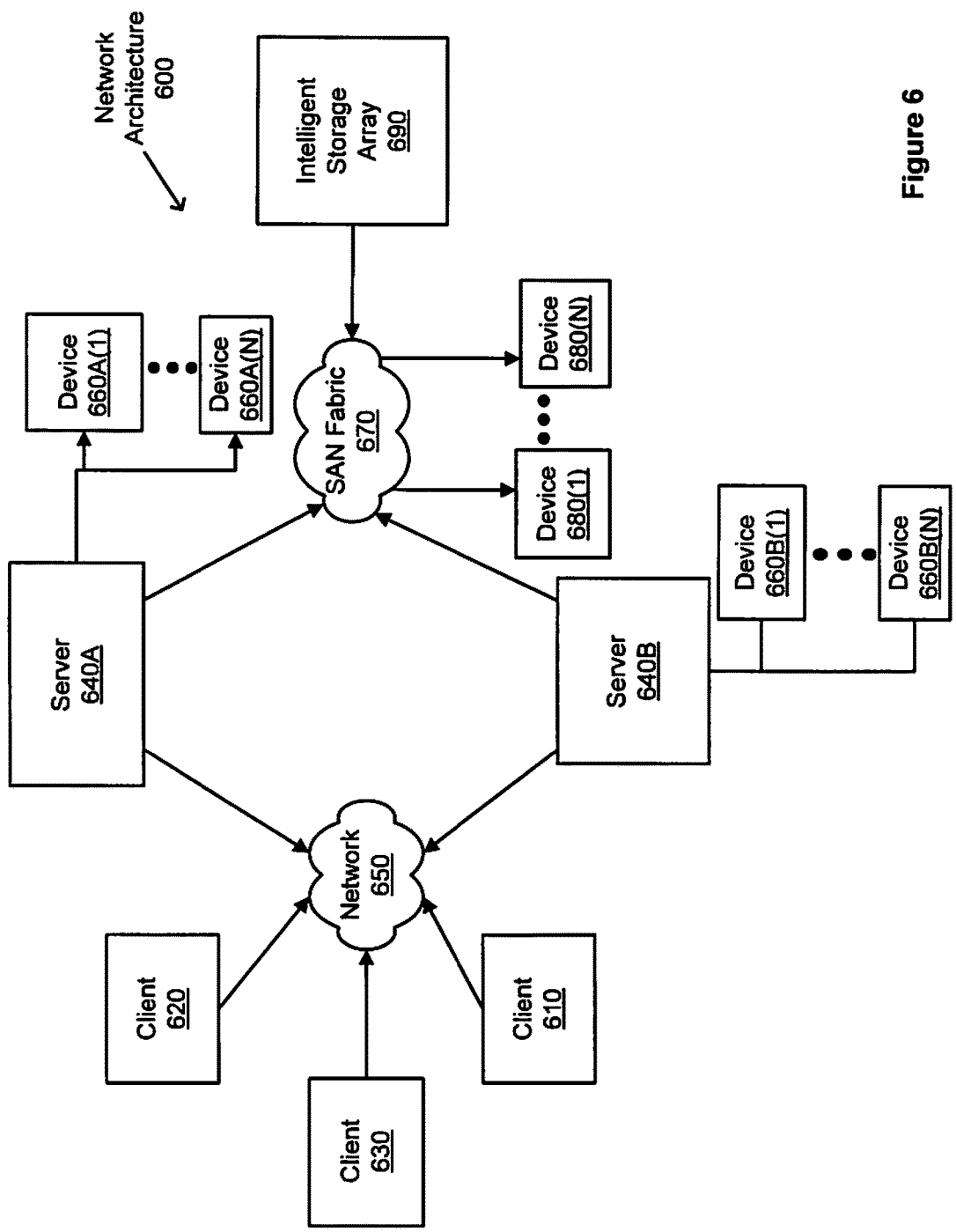
FIG. 6 is a block diagram depicting a network architecture suitable for deploying embodiments of the present invention.

FIG. 6 is a block diagram depicting a network architecture 600 in which client systems 610, 620 and 630, as well as storage servers 640A and 640B (any of which can be implemented using computer system 510), are coupled to a network 650. Storage server 640A is further depicted as having storage devices 660A(1)-(N) directly attached, and storage server 640B is depicted with storage devices 660B(1)-(N) directly attached. Storage servers 640A and 640B are also connected to a SAN fabric 670, although connection to a storage area network is not required for operation of the invention. SAN fabric 670 supports access to storage devices 680(1)-(N) by storage servers 640A and 640B, and so by client systems 610, 620 and 630 via network 650. Intelligent storage array 690 is also shown as an example of a specific storage device accessible via SAN fabric 670.

With reference to computer system 510, modem 547, network interface 548 or some other method can be used to provide connectivity from each of client computer systems 610, 620 and 630 to network 650. Client systems 610, 620 and 630 are able to access information on storage server 640A or 640B using, for example, a web browser or other client software (not shown). Such a client allows client systems 610, 620 and 630 to access data hosted by storage server 640A or 640B or one of storage devices 660A(1)-(N), 660B(1)-(N), 680(1)-(N) or intelligent storage array 690. FIG. 6 depicts the use of a network such as the Internet for exchanging data, but the present invention is not limited to the Internet or any particular network-based environment.

Other Embodiments

The present invention is well adapted to attain the advantages mentioned as well as others inherent therein. While the present invention has been depicted, described, and is defined by reference to particular embodiments of the invention, such references do not imply a limitation on the invention, and no such limitation is to be inferred. The invention is capable of considerable modification, alteration, and equivalents in form and function, as will occur to those ordinarily skilled in the pertinent arts. The depicted and described embodiments are examples only, and are not exhaustive of the scope of the invention.

The foregoing describes embodiments including components contained within other components (e.g., the various elements shown as components of computer system 510). Such architectures are merely examples, and, in fact, many other architectures can be implemented which achieve the same functionality. In an abstract but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality.

The foregoing detailed description has set forth various embodiments of the present invention via the use of block diagrams, flowcharts, and examples. It will be understood by those within the art that each block diagram component, flowchart step, operation and/or component illustrated by the use of examples can be implemented, individually and/or collectively, by a wide range of hardware, software, firmware, or any combination thereof.

The present invention has been described in the context of fully functional computer systems; however, those skilled in the art will appreciate that the present invention is capable of being distributed as a program product in a variety of forms, and that the present invention applies equally regardless of the particular type of signal bearing media used to actually carry out the distribution. Examples of signal bearing media include computer-readable storage media, transmission type media such as digital and analog communications links, as well as media storage and distribution systems developed in the future.

The above-discussed embodiments can be implemented by software modules that perform certain tasks. The software modules discussed herein may include script, batch, or other executable files. The software modules may be stored on a machine-readable or computer-readable storage media such as magnetic floppy disks, hard disks, semiconductor memory (e.g., RAM, ROM, and flash-type media), optical discs (e.g., CD-ROMs, CD-Rs, and DVDs), or other types of memory modules. A storage device used for storing firmware or hardware modules in accordance with an embodiment of the invention can also include a semiconductor-based memory, which may be permanently, removably or remotely coupled to a microprocessor/memory system. Thus, the modules can be stored within a computer system memory to configure the computer system to perform the functions of the module. Other new and various types of computer-readable storage media may be used to store the modules discussed herein.

The above description is intended to be illustrative of the invention and should not be taken to be limiting. Other embodiments within the scope of the present invention are possible. Those skilled in the art will readily implement the steps necessary to provide the structures and the methods disclosed herein, and will understand that the process parameters and sequence of steps are given by way of example only and can be varied to achieve the desired structure as well as modifications that are within the scope of the invention. Variations and modifications of the embodiments disclosed herein can be made based on the description set forth herein, without departing from the scope of the invention.

Consequently, the invention is intended to be limited only by the scope of the appended claims, giving full cognizance to equivalents in all respects.

Although the present invention has been described in connection with several embodiments, the invention is not intended to be limited to the specific forms set forth herein. On the contrary, it is intended to cover such alternatives, modifications, and equivalents as can be reasonably included within the scope of the invention as defined by the appended claims.

What is claimed is:

1. A method comprising:
   receiving, at a server, a first inventory item value and a second inventory item value from a first remote node associated with a first node identifier, wherein the first inventory item value identifies a first item installed on the first remote node, the first inventory item value is shorter than first identifying information associated with the first item, the second inventory item value identifies a second item installed on the first remote node, the second inventory item value is shorter than second identifying information associated with the second item, and
   the first and second inventory item values are generated from the first and second identifying information respectively using a hash function;
   during the receiving of values from the remote nodes, executing a bandwidth conservation by the server, by determining, by the server, that an entry for the first inventory item value is not stored in an inventory item list and that an entry for the second inventory item value is stored in the inventory item list, wherein the inventory item list is maintained by the server, the inventory item list comprises inventory item values corresponding to items installed on a plurality of remote nodes, the entry for the second inventory item value is associated with a second node identifier of a second remote node, and indicates that the second item is installed on the second remote node, and the determining comprises the server comparing, using a processor of the server, the first inventory item value with a plurality of entries in the inventory item list;
   responsive to determining that the entry for the first inventory item value is not stored in the inventory item list, scheduling, by the server, a time for a request;
   requesting, by the server, the first identifying information from the first remote node at the scheduled time; and
   creating, by the server, a first new entry in the inventory item list, wherein the first new entry comprises the first inventory item value and the first identifying information received from the first remote node in response to the requesting, and the creating comprises storing the first inventory item value in a first memory location and storing the first identifying information in a second memory location; and
   responsive to determining that the entry for the second inventory item value is stored in the inventory item list, creating, by the server, a second new entry in the inventory item list to be associated with the first node identifier of the first remote node, wherein the second new entry comprises the second inventory item value, and indicates that the second item is installed on the first remote node.

2. The method of claim 1 wherein the first and second item values uniquely identify the corresponding first and second items installed on the first remote node.

3. The method of claim 2 wherein the first inventory item value is generated using the first identifying information, and the first identifying information uniquely identifies the corresponding first item installed on the first remote node.

4. The method of claim 3, wherein when the corresponding first item is a software item, the first identifying information comprises a name, a manufacturer identifier, and a version number of the software item; and when the corresponding first item is a hardware item, the first identifying information comprises one or more of a unique device identifier, a hardware item type, a name of the hardware item, and a manufacturer of the hardware item.

5. The method of claim 3 further comprising transmitting the inventory item list to another server to identify one or more remote nodes based on information stored in the inventory item list and assign tasks to the identified remote nodes.

6. The method of claim 2 wherein each of the first and second inventory item values is a globally unique identifier (GUID) or an integer value.

7. The method of claim 1 further comprising:
storing the first and second inventory item values in entries associated with the first node identifier of the first remote node.

8. The method of claim 7 wherein the first node identifier of the first remote node is unique with respect to any other node in a network associated with the first remote node.

9. The method of claim 8 wherein the first node identifier of the first remote node is generated using one or more of the first remote node's MAC address, UUID, and serial number in sufficient combination to uniquely identify the first remote node.

10. The method of claim 9 wherein the first node identifier of the first remote node is generated using the hash function.

11. A non-transitory computer-readable storage medium comprising:
a first set of instructions, executable by a processor of a server, configured to receive, at the server, a first inventory item value and a second inventory item value from a first remote node associated with a first node identifier, wherein the first inventory item value identifies a first item installed on the first remote node, the first inventory item value is shorter than first identifying information associated with the first item, the second inventory item value identifies a second item installed on the first remote node, the second inventory item value is shorter than second identifying information associated with the second item, and the first and second inventory item values are generated from the first and second identifying information respectively using a hash function;
a second set of instructions, executable by the processor, configured to, during the receiving of values from the remote node, execute a bandwidth conservation by the server, by determining that an entry for the first inventory item value is not stored in an inventory item list maintained by the server and that an entry for the second inventory item is stored in the inventory item list, wherein the inventory item list comprises inventory item values corresponding to items installed on a plurality of remote nodes, the entry for the second inventory item value is associated with a second node identifier of a second remote node, and indicates that the second item is installed on the second remote node, and the determining comprises the server comparing, using the processor, the first inventory item value with a plurality of entries in the inventory item list;
a third set of instructions, executable by the processor, configured to:
responsive to determining that the entry for the first inventory item value is not stored in the inventory item list, schedule, by the server, a time for a request;

request, from the first remote node, the first identifying information at the scheduled time; and
create, by the server, a first new entry in the inventory item list, wherein the first new entry comprises the first inventory item value and the first identifying information received from the first remote node in response to the requesting, and creating the first new entry comprises storing the first inventory item value in a first memory location and storing the first identifying information in a second memory location; and
a fourth set of instructions, executable by the processor, configured to:
responsive to determining that the entry for the second inventory item value is stored in the inventory item list, create, by the server, a second new entry in the inventory item list to be associated with the first node identifier of the first remote node, wherein the second new entry comprises the second inventory item value, and indicates that the second item is installed on the first remote node.

12. The non-transitory computer-readable storage medium of claim 11 wherein the first and second item values uniquely identify the corresponding first and second items installed on the first remote node.

13. The non-transitory computer-readable storage medium of claim 11 further comprising:
a fifth set of instructions, executable by the processor, configured to store the first and second inventory item values in entries associated with the first node identifier of the first remote node.

14. An apparatus comprising:
a processor;
an inventory database coupled to the processor and configured to store an inventory item list;
an inventory recording module configured to execute on the processor and further configured to:
receive, at the apparatus, a first inventory item value and a second inventory item value from a first remote node associated with a first node identifier, wherein the first inventory item value identifies a first item installed on the first remote node, the first inventory item value is shorter than first identifying information associated with the first item, the second inventory item value identifies a second item installed on the first remote node, the second inventory item value is shorter than second identifying information associated with the second item, and the first and second inventory item values are generated from the first and second identifying information respectively using a hash function; and
store inventory information from the first remote node in the inventory database; and an inventory item resolution module configured to execute on the processor of the apparatus and further configured to:
during the receiving of values from the remote nodes, execute a bandwidth conservation by the server, by determining that an entry for the first inventory item value is not stored in the inventory item list, and that an entry for the second inventory item value is stored in the inventory item list, wherein the inventory item list comprises inventory item values corresponding to items installed on a plurality of remote nodes, the entry for the second inventory item value is associated with a second node identifier of a second remote node, and indicates that the second item is installed on the second remote node, and the determining comprises comparing, using the processor, the first inventory item value with a plurality of entries in the inventory item list;

responsive to determining that the entry for the first inventory item value is not stored in the inventory item list, schedule, by the apparatus, a time for a request;

request, by the apparatus, the first identifying information from the first remote node at the scheduled time; and create, by the apparatus, a first new entry in the inventory item list, wherein the first new entry comprises the first inventory item value and the first identifying information received from the first remote node, and creating the first new entry comprises storing the first inventory item value in a first memory location and storing the first identifying information in a second memory location; and responsive to determining that the entry for the second inventory item value is stored in the inventory item list, create, by the apparatus, a second new entry in the inventory item list to be associated with the first node identifier of the first remote node, wherein the second new entry comprises the second inventory item value, and indicates that the second item is installed on the first remote node.

15. The apparatus of claim 14 wherein the first and second inventory item values uniquely identify the corresponding first and second items installed on the first remote node.

16. The apparatus of claim 15, wherein the first inventory item value is generated using the first identifying information, and the first identifying information uniquely identifies the corresponding first item installed on the first remote node.

17. The apparatus of claim 16 wherein the inventory item resolution module is further configured to transmit the inventory item list to another server to identify one or more remote nodes based on information stored in the inventory item list and assign tasks to the identified remote nodes.

18. The apparatus of claim 14 wherein the inventory recording module is further configured to:

store the first and second inventory item values in entries associated with the first node identifier of the first remote node.

19. The apparatus of claim 18 wherein the first node identifier of the first remote node is unique with respect to any other node in a network associated with the first remote node.

20. The apparatus of claim 18 wherein the first node identifier of the first remote node is generated using the hash function.

21. The method of claim 1, wherein requesting the first identifying information comprises:

transmitting an information request to the first remote node, wherein the information request identifies the first inventory item using the first inventory item value, and further comprising:

receiving, from the first remote node, the first identifying information related to the first inventory item.

* * * * *